United States Patent [19]

Jones et al.

[11] Patent Number: 5,286,356

[45] Date of Patent: Feb. 15, 1994

[54] METHOD FOR SAMPLE ANALYSIS USING CAPILLARY ELECTROPHORESIS

[75] Inventors: William R. Jones, Northborough; Martin Fuchs, Uxbridge; Michael Merion, Upton, all of Mass.

[73] Assignee: Millipore Corporation, Bedford, Mass.

[21] Appl. No.: 6,434

[22] Filed: Jan. 21, 1993

[51] Int. Cl.$^5$ ............................................. C25B 7/00
[52] U.S. Cl. .................................. 204/182.8; 356/344
[58] Field of Search ...................... 204/182.8; 356/344

[56] References Cited

U.S. PATENT DOCUMENTS 5,015,350   5/1991   Wiktorowicz .................. 204/182.8

OTHER PUBLICATIONS

Gebauer et al. "Sample self-stacking in zone electrophoresis. Theoretical description of the zone electrophoretic separation of minor compounds in the presence of bulk amounts of a sample component with high mobility and like charge." *Journal of Chrom.*, 608(1992) 47–57.

CA 84(25): 176087g. A highly regulated, recording constant power, voltage, and current supply for electrophoresis and isoelectric focusing. 1976.

CA 84(3):14278t Accelerated liquid isolectric focusing using a direct current source that maintains constant power. 1976.

*Primary Examiner*—T. Tung
*Assistant Examiner*—Cybille Delacroix-Muirheid
*Attorney, Agent, or Firm*—Andrew T. Karnakis; Paul J. Cook

[57] ABSTRACT

A method for performing capillary electrophoresis with improved regularity of migration time of the analytes is disclosed. A capillary electrophoresis system includes a fused silica capillary, a high voltage power supply, electrolyte reservoirs at both ends of the capillary, means for injecting a sample, and a detector. After separation, analytes within the sample are identified by comparing their migration time with the migration time of internal or external standards. Since migration times are dependent on the concentration of the injected sample, identification of unknown analytes can often be difficult or subject to error without the use of such standards. These problems associated with concentration dependent migration time are substantially eliminated by using a combination of high voltage power supply running modes (i.e. constant current, constant voltage or constant power) during the course of the analysis. The control of the high voltage power supply can either be set before a run begins, or controlled directly using feedback from the separation in real time.

13 Claims, 5 Drawing Sheets

METHOD FOR SAMPLE ANALYSIS USING CAPILLARY ELECTROPHORESIS

BACKGROUND OF THE INVENTION

Capillary electrophoresis (CF) has become a technique of great interest for the separation and analysis of many kinds of ionic species, including inorganic ions, biological mixtures such as proteins, peptides and nucleic acids, detergents, organic acids and many compounds of pharmaceutical nature. Capillary electrophoresis offers the benefits of high resolving power, rapid separations, ability to analyze very small volumes of sample and a desirable simplicity from the point of view of the apparatus required when compared to competing analytical techniques such as liquid chromatography.

The benefits of capillary electrophoresis mentioned above derive to a large extent from the use of narrow diameter capillary tubes in the practice of capillary electrophoresis. The narrow diameter tubes permit efficient removal of the heat generated in the separation process and prevent convective mixing which would degrade the separating power. The narrow diameter tubes also allow high voltages to be used to generate the electric field in the capillary while limiting current flow and hence heat generation. The electric field in the capillary tube which provides the driving force for the separation is produced by the application of high voltage power to the ends of the capillary. The high voltage power is generally applied from a high voltage power supply operating at an operator selected constant voltage during the separation.

Variations on the application of constant voltage operation have been proposed in the past. For example, in order to overcome drift in certain detectors used in CE, Morris et al applied an AC voltage superimposed on a constant DC voltage to drive a CE separation, as described in U.S. Pat. No. 4,909,919. The AC voltage modulates the velocity of the migrating sample components and the detector signal is synchronously demodulated to cancel out drift due for example to temperature fluctuations in the capillary. Likewise, in applications involving the separation of DNA fragments in gel containing capillaries, the high voltage can be applied in a pulsed manner as described in U.S. Pat. No. 5,122,248. The pulsing of the applied voltage results in a greater degree of resolution of the closely related fragments, due to reorientation of analyte molecules in the separating medium during different phases of each pulse. However, in each of these illustrated examples, the average DC level of the output voltage from the power supply remains constant throughout the analysis.

In other cases, it may be preferable to operate the high voltage power supply at a selected level of current through the capillary tube during the entire separation. This is referred to as constant current operation. Takao Tsuda describes certain advantages of operating at a constant current in an article in the Journal of Liquid Chromatography, volume 12 (1989) page 2501, primarily related to the fact that the separation is less dependent on the temperature of the capillary in constant current operation. Similarly, constant power operation is also possible where the level of power dissipated in the capillary is held constant at a selected level.

The separation that occurs in capillary electrophoresis is generally monitored somewhere along the length of the capillary tube by a detector that responds with a signal that is proportional to the concentration at the monitoring point of the analyte(s) within the sample to be measured. Absorbance detectors are commonly used but other kinds of detectors are also possible, such as fluorescence, conductivity, electrochemical and the like. In some cases, the separating medium is modified prior to detection by the addition of reagents to label the analyte or by modifying the conductivity of the medium through ion exchange.

The detectors employed are to a greater or lesser extent non-specific. That is, they respond with an indication of the concentration of many different analytes thus not directly determining the identity of the analyte. In some cases, additional information is available to aid in identifying the sample components, such as when the detector is capable of measuring absorbance at multiple wavelengths so as to obtain an absorbance spectrum or ratios of absorbances at several wavelengths. Alternatively, the separated analytes can be collected as they emerge from the capillary and subjected to further analysis by other techniques. However, multiwavelength detection adds cost and complexity and spectral information may not be available if the analyte is transparent over the spectral range being measured and is being determined instead by an indirect absorbance measurement where the response is due to the displacement of an absorbing species in the separating medium. Post separation analysis by other techniques requires additional time and effort and is not always possible due to the small amount of sample analyzed by capillary electrophoresis.

The detector also permits the measurement of the migration time for each analyte and the migration time can be used to characterize each component of the sample mixture. For purposes herein, the migration time for each analyte is defined as the time period from the start of the analysis to the appearance at the detector of the concentration peak of that analyte. The migration time of each sample component can be compared to the migration times of known standards, and when combined with other knowledge about the origin and character of the sample, allow the identity of the sample components to be inferred. In order for the migration time to be useful, each analyte must appear in the separation at its characteristic migration time over the range of experimental conditions that the analysis is to be used for. In particular, the migration time of each analyte must remain essentially constant over the range of sample compositions that are likely to be encountered.

It is known that the migration time of each analyte tends to fluctuate depending on the composition of the sample. Petr Gebauer, Wolfgang Thormann and Petr Bocek provide a theoretical explanation of how such fluctuations can occur in an article in the Journal of Chromatography, volume 608 (1992) pp. 47-57. This article describes how the concentration of a major component in the sample can affect the migration time of minor sample components by amounts in the tens of percent and cautions that the record of each analysis must be evaluated with great care to avoid making a false determination of the identity of the analytes in the sample. However, the authors do not propose solutions to prevent migration times from varying. Also, neither the patent cited above concerning the application of pulsed voltage nor that describing the imposition of an AC voltage on the DC separation voltage addressess the problem of migration time variation caused by changing sample composition.

In certain applications, the effect of sample composition changes can be magnified, as when it is desired to maximize the sensitivity of a capillary electrophoresis analysis. For example, it may be advantageous for the sample mixture to be analyzed to be dissolved in pure water or other very low conductivity medium rather than, for example, in the separating medium. This causes a phenomenon known as stacking to occur and permits a larger volume of sample mixture to be introduced into the capillary without undesirable broadening of the analyte concentration peaks. However, when the sample is dissolved in pure water to achieve this desirable enhancement in sensitivity, the migration time of the analytes becomes even more dependent on the sample composition.

It would thus be desirable to be able to use migration time as an identifying characteristic for sample components in CE and it would also be desirable to do this while also using the sensitivity enhancement that results from having the sample mixture dissolved in pure water or other low conductivity medium.

SUMMARY OF THE INVENTION

This and other shortcomings of capillary electrophoresis systems of the prior art are addressed by the present invention which includes a capillary electrophoresis system incorporating novel methods of control of the high voltage power supply. The control of the high voltage power supply is characterized by initiating a change in its output condition during the analysis, such as the sequential use of two or more of the following high voltage operating modes in a single analysis: constant current, constant voltage, and constant power.

The change in output condition is appropriately timed to effectuate the substantially complete elimination of migration time changes that are due to varying concentrations of ions in the sample. The timing and control of the switching of the power supply output condition may be determined by calculation prior to the analysis and/or initiated by feedback control from the capillary during the analysis.

In one embodiment, the first time segment of the analysis is conducted in the constant current mode, followed by the remainder of the analysis being conducted in the constant voltage mode. The length of the time segments is determined prior to analysis. Alternatively, the first segment of the analysis is conducted in the constant voltage mode, followed by the remainder of the analysis being conducted in the constant current mode. Again, the segment length is determined prior to analysis. In a further refinement of the embodiment, on-line migration time measurements of an internal standard are used to determine optimum switching times of the high voltage power supply thereby eliminating residual migration time shifts of the analytes to be measured.

DETAILED DESCRIPTION OF THE EMBODIMENTS OF THE INVENTION

Figure 1:
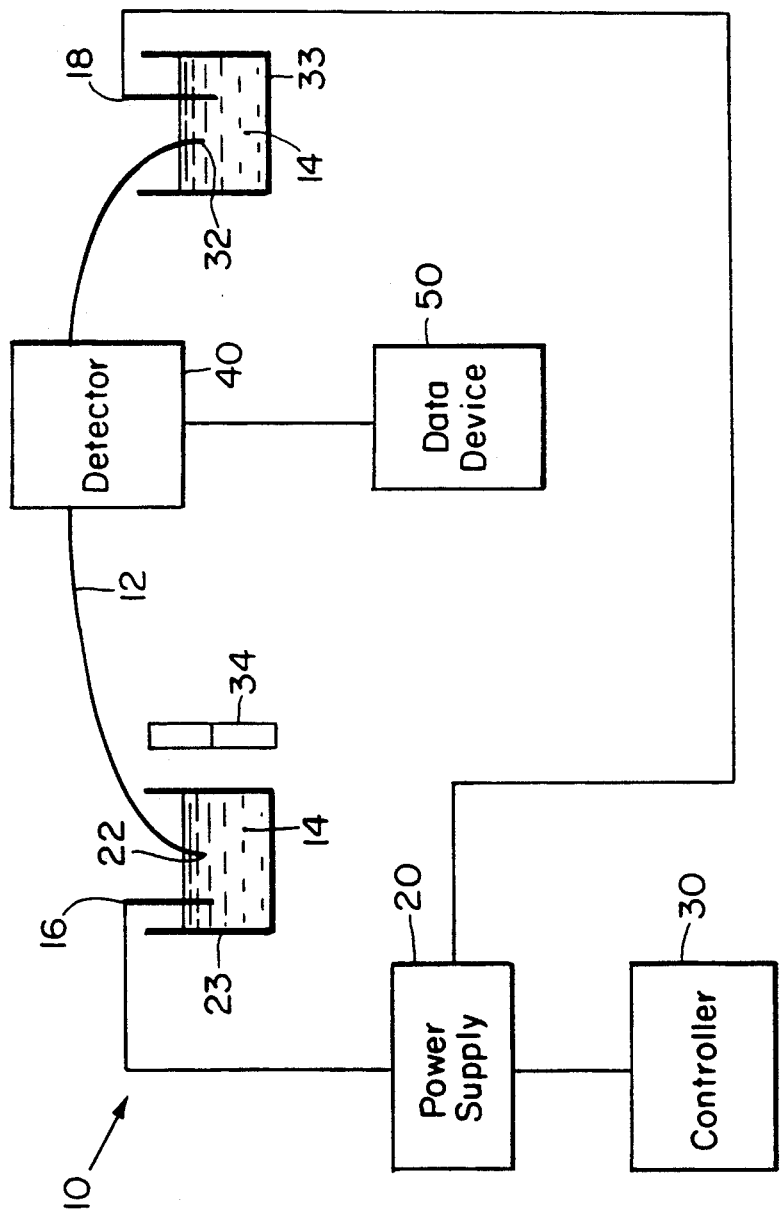
FIG. 1 is a block diagram of a CE system in accordance with the invention.
Figure 2A:
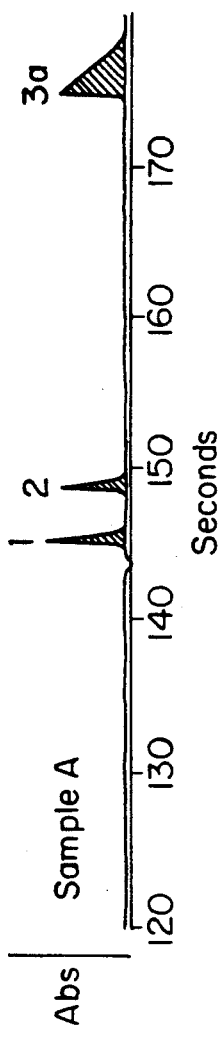
FIGS. 2a–d are a series of graphs showing the separation of a mixture of ions, with the concentration of one of the ions in the mixture varying, by the CE system of FIG. 1 run under constant voltage conditions.
Figure 2B:
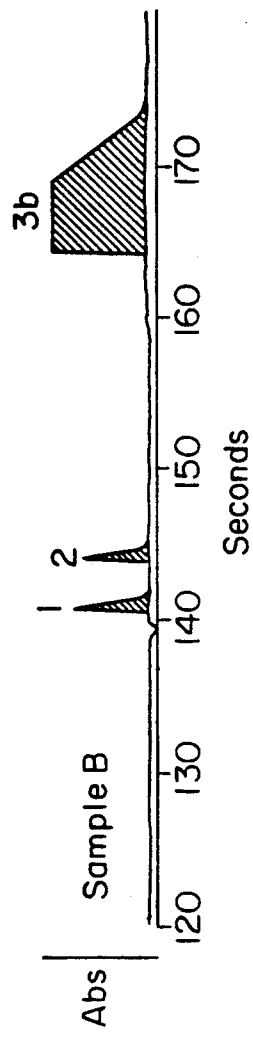
Figure 2C:
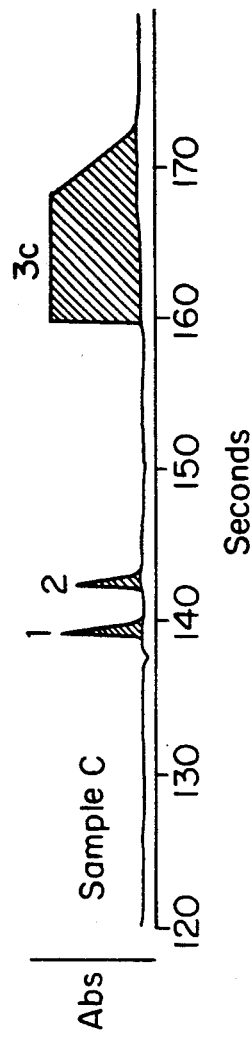
Figure 2D:
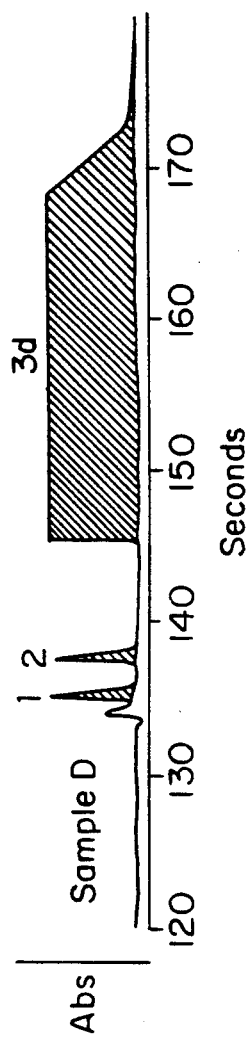
Figure 3A:
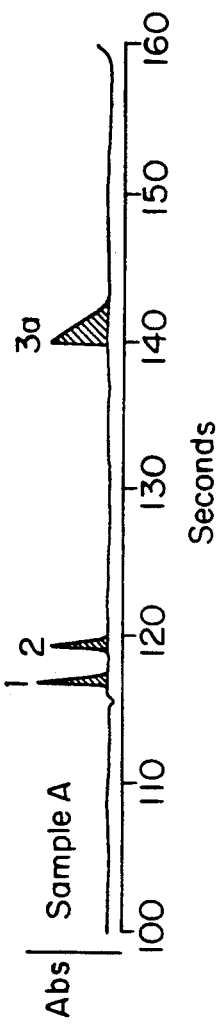
FIGS. 3a–d are a series of graphs showing the separation of the same mixture of ions as in FIGS. 2a–d but with the CE system run under constant current conditions.
Figure 3B:
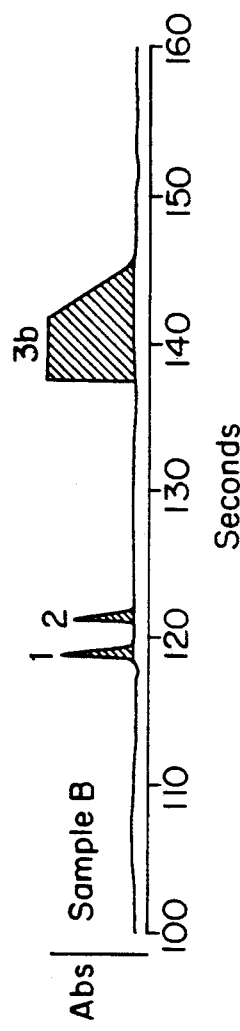
Figure 3C:
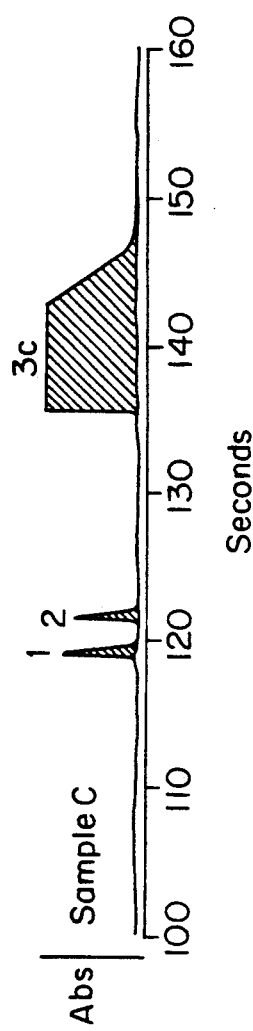
Figure 3D:
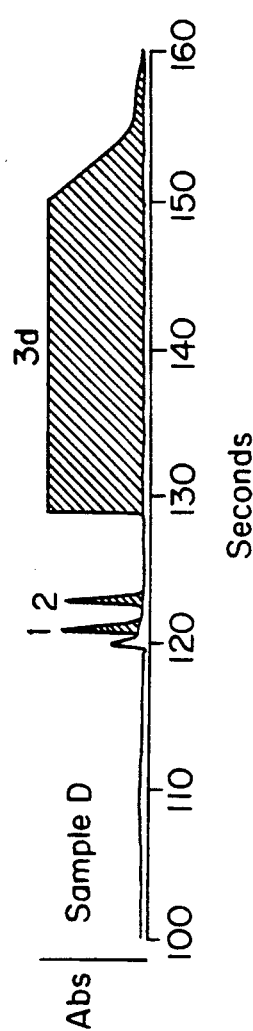
Figures 4A, 4B, 4C, 4D:
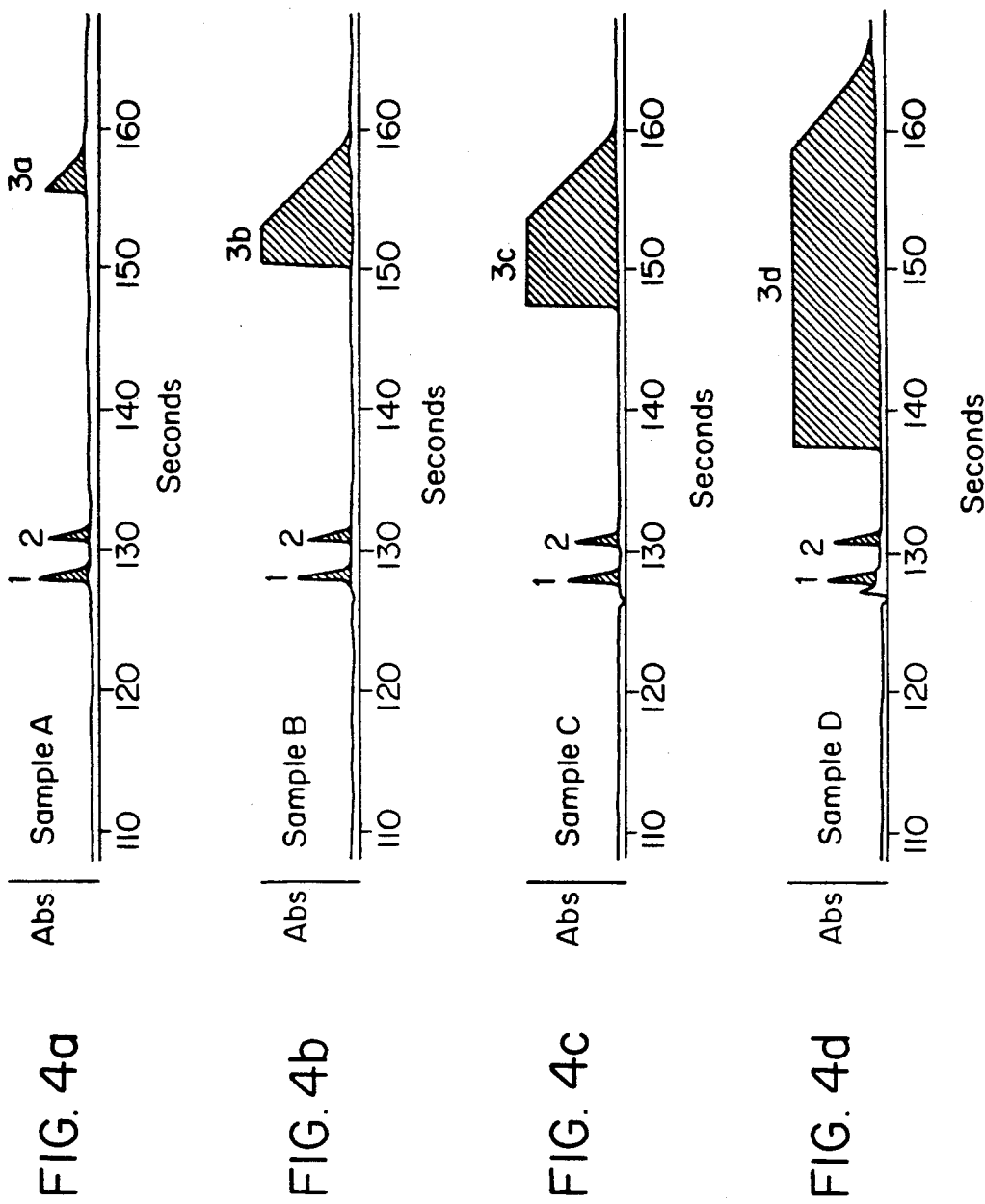
FIGS. 4a–d are a series of graphs showing the improved separation results for the same mixture of ions as in FIGS. 2a–d and FIGS. 3a–d when the CE system is operated in accordance with one embodiment of the present invention.

FIG. 1 shows a block diagram of a CE system 10 of the present invention. The system includes a fused silica capillary 12 with an inside diameter having a range of from about 5 to about 500 $\mu$m, and preferably from 25 to 100 $\mu$m, having an inlet end 22 and an outlet end 32. Each of the ends of the capillary tube is immersed in respective inlet and outlet reservoirs 23, 33 containing an electrolyte solution 14 which extends to fill the inside volume of the capillary. Contacting the electrolyte solution in the reservoirs are separate electrodes 16, 18 that are connected to the output terminals of a high voltage power supply 20. The high voltage power supply output is set by a controller 30.

To perform an analysis, a sample solution contained in vial 34 is introduced into the capillary 12 by placing the inlet end 22 of the capillary into the sample solution in vial 34 after which a hydrostatic pressure in the range from 0.1 to 1 psig is applied to the sample solution with respect to the outlet end 32 of the capillary. Alternatively, the high voltage power supply 20 can be activated for a period of time after the inlet end 22 of the capillary has been immersed in the sample solution in vial 34, with the resulting electric field causing sample to migrate into the capillary.

After a sufficient amount of sample is introduced, the inlet end 22 of the capillary 12 is returned to the electrolyte reservoir 23. High voltage is then applied by the power supply 20 to the electrodes 16, 18 contacting the electrolyte solution 14 so that the voltage is applied from one end of the capillary tube to the other. The controller 30 can signal the power supply to apply the voltage in different modes. The term "mode(s)" is used to denote the power supply output regulation and is intended to encompass constant voltage, constant current and constant power operation. Further, the controller can cause the power supply to change mode or output level during the analysis.

The high voltage creates an electric field within the capillary 12 that causes the components of the sample to move along the length of the capillary tube. The velocity of motion of each component is a function of its molecular size and shape, the electrical charge that each molecule carries, the viscosity of the electrolyte solution in the capillary tube, the magnitude of the electric field in the capillary and the rate of bulk flow caused by electroosmosis. A UV/Vis absorbance detector 40 is positioned at any convenient location along the length of the capillary, preferably near the outlet end 32 and is adapted to measure the components of the sample in known fashion through the walls of the capillary. As individual sample components pass through the detector segment of the capillary, the detector output signal changes in a manner that is related to the concentration of analyte molecules passing through that segment of the capillary tube. The output signal from the detector is connected to a data collection device 50.

We have studied the effect of sample composition on the migration time of the components of the sample and found that the effect of sample composition can be correlated to the mode of operation of the high voltage power supply. This is illustrated in FIGS. 2a–d and FIGS. 3a–d. A series of separations of the inorganic anions, chloride, sulfate and fluoride, were performed using an electrolyte of known composition and conductivity where the concentrations of chloride and sulfate in the sample solution were held constant but the concentration of fluoride was varied.

Four samples (designated Sample A, B, C and D respectively on the two sets of graphs) were composed. The composition of each analyte of interest, the numbered peak corresponding to each separated analyte shown on the graphs as well as the measured conductivity for each sample and of the electrolyte is given below.

|  | Ion Composition |  | Peak Number | Conductivity ($\mu$S @ 24° C.) |
| --- | --- | --- | --- | --- |
| Sample A | Chloride | 4 ppm | 1 | 56 |
|  | Sulfate | 4 ppm | 2 |  |
|  | Fluoride | 4 ppm | 3a |  |
| Sample B | Chloride | 4 ppm | 1 | 203 |
|  | Sulfate | 4 ppm | 2 |  |
|  | Fluoride | 30 ppm | 3b |  |
| Sample C | Chloride | 4 ppm | 1 | 356 |
|  | Sulfate | 4 ppm | 2 |  |
|  | Fluoride | 60 ppm | 3c |  |
| Sample D | Chloride | 4 ppm | 1 | 1519 |
|  | Sulfate | 4 ppm | 2 |  |
|  | Fluoride | 300 ppm | 3d |  |
| Electrolyte | — |  | — | 1131 |

The CE system 10 used for these separations was a Quanta ™ 4000 equipped with a Model 860 data system, commercially available from the Waters Chromatography Division of Millipore Corporation. The system was used with a Waters AccuSep ™ fused silica capillary 12 which had a 75 $\mu$m inner diameter and was 60 cm long. The system was operated under the following conditions to obtain the separations shown in FIGS. 2a–d:

Electrolyte: 5 mM sodium chromate, 0.5 mM tetradecyltrimethylammonium bromide (TTAB), pH 8.0
Sample Introduction: 9.8 cm hydrostatic head for 30 seconds
Power Supply: negative polarity
Potential: 20 kV
Detector: UV Absorbance located at 52 cm from inlet end
Wavelength: 254 nm
Detector Time Constant: 0.1 second
Data Acquisition: 20 pts/sec.

As indicated, FIGS. 2a–d show the results obtained when the separations were performed according to prior art techniques where the high voltage power was applied in the constant voltage mode. One sees that the migration time of both chloride and sulfate decreases as the concentration of fluoride is increased. In comparing FIGS. 2a and 2b we see that the migration time of sulfate in FIG. 2b approximates the migration time of chloride in FIG. 2a. This is undesirable since it makes identification of the chloride and sulfate concentration peaks difficult, particularly when there are additional components in the sample.

The separations shown in FIGS. 3a–d were run under the same conditions as above except the power supply 20 was operated in constant current mode at 20 $\mu$A. Here the effect of increasing the fluoride concentration is to cause the migration time of both chloride and sulfate to increase. Though opposite in direction, this effect is equally undesirable.

We have found that by properly using more than one power supply operating mode in combination during a single analysis, the effects illustrated above can be made to cancel resulting in essentially no change in migration time for the analytes of interest as the sample composition varies. For example, if the system 10 is operated in constant current mode for a period of time, the optimum length of which can be experimentally determined, and then switched to constant voltage operation for the remainder of the separation, the resulting migration times become substantially independent of sample composition.

As previously mentioned, using the prior art methodology, the migration times of the components of the sample are dependent on the composition of the sample. For the example above, in constant voltage mode, the migration times become shorter as the overall concentration of ions in the sample increases (and hence the conductivity of the sample increases), whereas in constant current mode the reverse happens, namely the migration times become longer as the overall concentration of ions in the sample increases.

These observations can be understood on the basis of the magnitude of the electric field in the capillary 12 and in the variation of that field along the length of the capillary. The electric field, acting on the charge that each ion carries, creates the driving force that propel the ions in electrophoresis. Any changes in the electric field or its distribution will therefore be reflected in changes in the velocity of migration of the ions in the sample.

The following example will show how the sample composition influences the migration time of the components of the sample. The same four samples (A,B,C and D) corresponding to the samples shown in FIGS. 2a–d and FIGS. 3a–d, all containing the anions chloride, sulfate and fluoride (each as the sodium salt) with the concentration of fluoride varying as shown in Table I, were analyzed by the CE system 10.

TABLE I

| Sample | Sample and Electrolyte Composition | | | |
| --- | --- | --- | --- | --- |
|  | [Cl] | [SO4] | [F] | Conductivity |
| A | 4 ppm | 4 ppm | 4 ppm | 55 ($\mu$S/cm) |
| B | 4 | 4 | 30 | 203 |
| C | 4 | 4 | 60 | 356 |
| D | 4 | 4 | 300 | 1519 |
| electrolyte: | 5 mM sodium chromate, 0.5 mM TTAB, pH8 | | | 1131 ($\mu$S/cm) |

Sample introduction into the capillary 12 is by 9.8 cm of hydrostatic head applied for 30 seconds. The capillary is 60 cm long with an inner diameter of 75 $\mu$m.

The length of the sample zone (i.e. the length of the plug of sample solution that flows into the capillary during the 30 seconds that 9.8 cm of hydrostatic head is applied) can be calculated. The average velocity, $v_{avg}$, of the flow is given by the following equation:

$$v_{avg} = \Delta p \, d^2 / 32 \eta L$$

where $\Delta p$ is the pressure difference between the two ends of the capillary ($\Delta p = 9.61 \times 10^3$ g/cm sec² at 9.8 cm head), d is the capillary inner diameter (75 $\mu = 7.5 \times 10^{-3}$ cm), $\eta$ is the viscosity of the solution in the capillary ($10^{-2}$ g/cm sec for water at 20° C.), and L is the capillary length (60 cm). Substituting these values:

$$v_{avg} = 2.82 \times 10^{-2} \text{ cm/sec.}$$

The sample zone length, $L_s$, is given by the product of the velocity and the duration of the sample introduction period.

$$L_s = (2.82 \times 10^{-2})(30) = 0.842 \text{ cm.}$$

The 0.842 cm length of the sample zone is big by CE standards, representing 1.4% of the 60 cm capillary length. It is possible in this case without undesirable broadening of the sample peaks because the samples are dissolved in pure water. This means that the analyte bands, which move at velocities different from that of the sample zone, will sharpen as they migrate into the electrolyte.

The electrical resistance of a capillary filled with electrolyte is calculated and the effect on the resistance of introducing the sample zone for the different sample compositions is determined. The measured value of the electrolyte conductivity, $\sigma$, is 1131 $\mu$S/cm. $R_{cap}$, the resistance of the capillary, is determined from the following equation (with terms and values as above):

$$\begin{aligned} R_{cap} &= L/\sigma\pi(d/2)^2 \\ &= 60/(113 \times 10^{-6})\pi(3.75 \times 10^{-3})^2 \\ &= 1.20 \times 10^9 \Omega \end{aligned}$$

Similarly one can calculate the resistance, $R_s$, of the 0.842 cm sample zone for each sample as well as the resistance of the remainder of the capillary, $R_{el}$, and the total resistance of the two zones (i.e. sample and electrolyte) in series, $R_{tot}$.

TABLE II

| Resistances of the Zones in the Capillary (ohms). | | | |
|---|---|---|---|
| Sample | $R_s$ | $R_{el}$ | $R_{tot}$ |
| A | $3.47 \times 10^8$ | $1.18 \times 10^9$ | $1.53 \times 10^9$ |
| B | $9.39 \times 10^7$ | $1.18 \times 10^9$ | $1.27 \times 10^9$ |
| C | $5.37 \times 10^7$ | $1.18 \times 10^9$ | $1.23 \times 10^9$ |
| D | $1.26 \times 10^7$ | $1.18 \times 10^9$ | $1.195 \times 10^9$ |

Since the two zones are electrically in series, $R_{tot}$ is given by the sum of $R_s$ and $R_{el}$. $R_{el}$ is less than $R_{cap}$ because the length of electrolyte is shorter by the length of the sample zone.

The sample zone with low fluoride concentrations have higher electrical resistance. It can be seen that the dilute samples have a significant effect on the overall capillary resistance. This means, for example, that in constant voltage operation, the capillary current will be significantly lower when dilute sample is introduced.

The electric field strength in the sample zone and in the rest of the capillary for the different samples and for both constant voltage and constant current operation can be calculated from the equation below:

$$E = IR/L$$

where E is the electric field in volts/cm, I is the capillary current (given by $V/R_{tot}$ in the constant voltage case, V being the voltage applied to the capillary), R is the resistance and L is the length of the zone.

The electric field values are shown in Table III. It is important to realize that a low conductivity sample zone never disappears even after the analyte ions have migrated out of the zone and been replaced by background electrolyte ions, but continues to traverse the length of the capillary. While the edges of the zone will blur due to diffusion, the sample solvent zone will maintain its identity and move through the capillary at the electroosmotic flow rate. Thus the impact of the sample zone on the field distribution in the capillary will be felt throughout the separation (if, as here, the sample zone elutes after the analyte ions) though the resistance of the zone does change somewhat as electrolyte ions and counterions replace analyte ions and counterions due to differences in the mobilities of these ions. Thus the current trace in constant voltage operation shows some rapid changes as the analytes migrate out of the sample zone and are replaced by background electrolyte and a more gradual change due to the diffusional blurring of the sample zone edges and a final value after the analytes have eluted but with the sample zone still in the capillary which is different for each of the sample levels.

TABLE III

| Electric Field Distribution in the Capillary (V/cm). | | | | |
|---|---|---|---|---|
| | Const. Voltage | | Const. Current | |
| Sample | $E_s$ | $E_{el}$ | $E_s$ | $E_{el}$ |
| A | 5390 | 260 | 6882 | 333 |
| B | 1756 | 313 | 1862 | 333 |
| C | 1037 | 323 | 1065 | 333 |
| D | 250 | 335 | 250 | 333 |

For constant current operation, Table III shows that as the sample becomes more conductive in going from sample A to sample D, the field in the sample zone, $E_s$, decreases. In the rest of the capillary, because the current is always held at the same level, the field, $E_{el}$, does not change. The overall effect is for migration times to get slightly longer. This is what is experimentally observed.

In the constant voltage case, the situation is a bit more complicated because of the way the applied voltage divides between the zones. As in the constant current case, the field in the sample zone decreases in going from sample A to sample D. But now, the field in the rest of the capillary increases as the field in the sample zone decreases. These changes have opposing effects on the migration time. Because the analytes traverse the sample zone quickly and spend the majority of the migration time in the electrolyte zone, the overall effect is for migration times to get shorter. Again, this is borne out experimentally.

There are several points to be made from these results. One is that in constant current operation, all the variability is in the sample zone field and hence in how fast the ions traverse this zone. This effect is illustrated by considering how long it takes chloride with a mobility of $7.9 \times 10^{-4}$ cm²/V sec to traverse the 0.842 cm sample zone. The results, determined by the equation below, are summarized in Table IV.

time = distance/velocity
= $L_S$/(mobility · electric field in sample zone)

TABLE IV

Time (seconds) for Chloride to Traverse Sample Zone

| Sample | Const. Current $E_s$ | time |
|---|---|---|
| A | 6882 | .15 |
| B | 1862 | .57 |
| C | 1065 | 1.00 |
| D | 250 | 4.26 |

As the fluoride concentration increases, it takes longer for the chloride ions to traverse the sample zone and hence the overall migration time becomes longer as well.

Another point is that the total resistance of the capillary changes with changes in sample conductivity as we have seen in Table II. This means that by measuring the current in constant voltage mode or voltage in constant current mode, one can measure the total resistance and from the resistance calculate the actual conductivity of the sample (this is done by reversing the calculations above leading to the total resistance). The value of the sample conductivity may be used in determining how to change the separation conditions during the analysis run to achieve migration times that are independent of sample composition. In constant voltage mode, for example, where low conductivity samples have slower migration times, one could increase the voltage partway into the separation with the amount of the increase depending on the measured sample conductivity. Such correction could also be applied on the basis of direct measurements of sample conductivity prior to the analysis. The value of the sample conductivity would enable the controller to determine from a lookup table stored in its memory the correct time point in the analysis run to effect the increase in separation voltage and the amount of increase to be applied.

Since the effect of changing sample composition on the migration time is in opposite directions for constant voltage and constant current operation, we have found that a particularly advantageous approach to achieving migration times that are independent of sample composition is to combine these modes. That is, by operating in one mode for part of the analysis time followed by a change to another mode for the remainder of the analysis time the opposing effects can result in a cancellation of the migration time variations. We have seen that in constant current mode, migration times increase as the sample becomes more concentrated (and hence more conductive) due to the decreasing field strength in the sample zone. We have also seen that in constant voltage mode, the field in the rest of the capillary increases as the sample becomes more concentrated leading to shorter migration times. By starting the analysis in constant current mode, followed by a change to constant voltage mode partway into the analysis time, the resulting migration times can be held substantially constant for the range of sample compositions provided the time of switching the mode is properly selected.

The application of this method to the analysis by the CE system 10 of FIG. 1 of the same series of samples as in FIGS. 2a–d and FIGS. 3a–d is shown in FIGS. 4a–d (with compositions, numbered peaks and conductivity as given previously). Here the initial segment of the analysis, 72 seconds in duration, is performed in the constant current mode at 20 μA. Then the controller changes the high voltage power supply operating mode so that the second segment of the analysis, lasting for the remainder of the analysis time, is performed in the constant voltage mode at 20 kV. The other conditions are the same as in FIGS. 2a–d. As can be seen from the results, the migration times for chloride and sulfate remain substantially unchanged as the concentration of fluoride in the sample is varied. As a result, the concentration peaks can now be easily identified.

Figure 5:
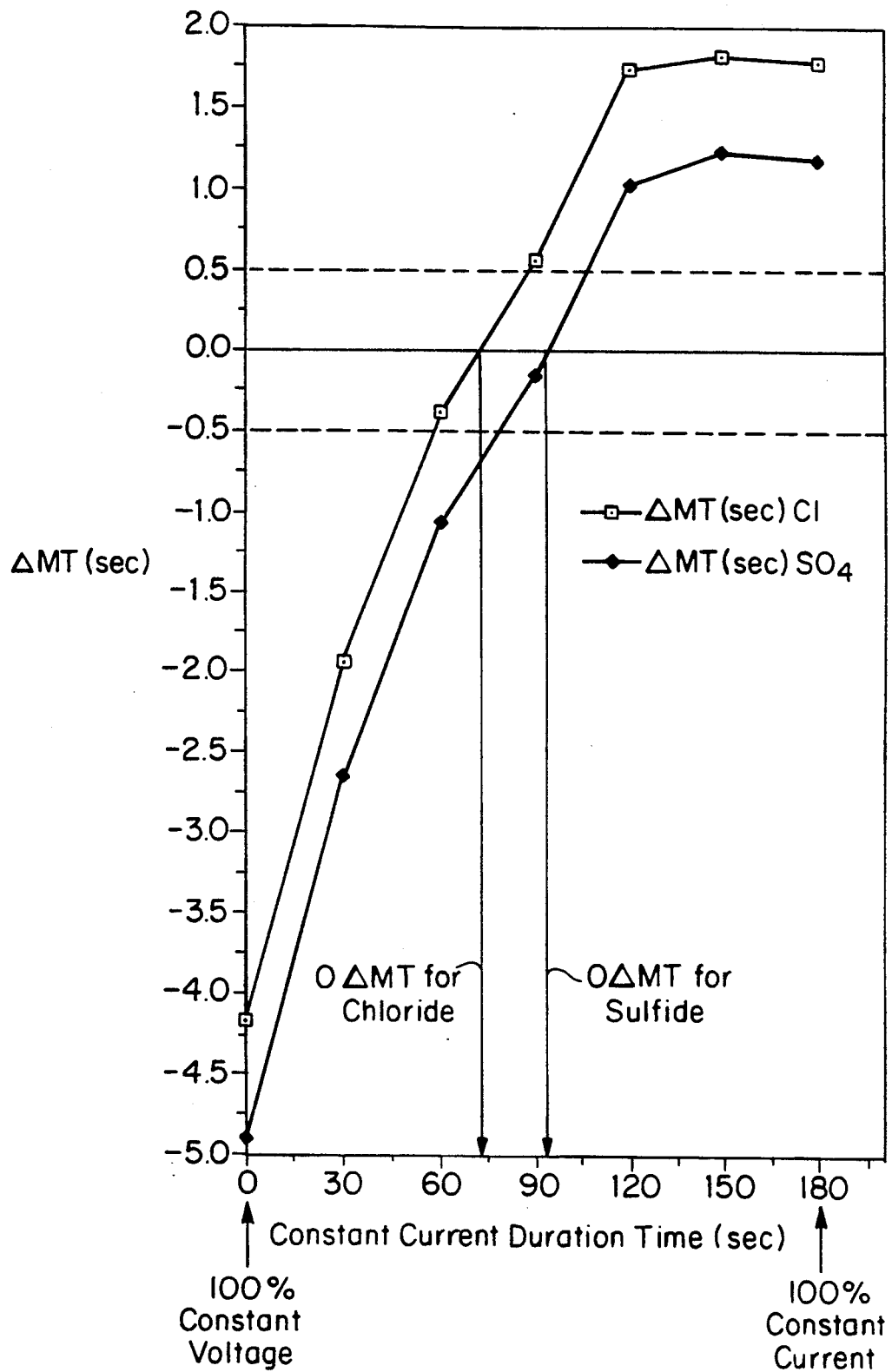
FIG. 5 is a graph showing changes in migration time for certain of the samples shown in FIGS. 2a–d and FIGS. 3a–d as a function of the time duration of constant current and constant voltage operation of the CE system of FIG. 1.

To illustrate the predetermination of the optimum time for switching the high voltage power supply operating mode, reference is made to the graph of FIG. 5. This graph plots the difference in migration time (ΔMT) for both chloride and sulfate ions. Each point on the graph represents a ΔMT measurement between sample D of FIG. 2d and FIG. 3d having a conductivity of 1519 μS/cm (i.e. a high concentration of fluoride) and sample A of FIG. 2a and FIG. 3a having a conductivity of 56 μS/cm (i.e. a low concentration of fluoride) as a function of the duration of time the CE system was run in the constant current mode at 20 μA, which was chosen as the first time segment of the analysis. The second time segment was performed in the constant voltage mode at 20 kV. The total analysis time was 180 seconds, and all the other conditions are the same as in FIGS. 2a–d. As shown at the extreme left (0 seconds constant current operation) and right (180 seconds constant current operation) of the abscissa of the graph, representing full duration constant voltage and constant current operation repectively, there are large differences in migration time for the ions between the two samples. Thus, for example, when run at full duration constant voltage, ΔMT for sulfate is about −4.8 seconds and ΔMT is about −4.3 seconds for chloride. The ΔMT's for these ions under full duration constant current operation are likewise large but now have a positive shift. Between these extremes are the points in time suitable for switched mode operation. At these points there is a gradual transition from the negative difference values of constant voltage operation to the positive difference values of constant current operation. By selecting a value of 72 seconds for the duration of the first time segment, the migration time differences are near zero for both chloride and sulfate ions.

Variations on this approach can be used to achieve the same result. For example, using the two modes (constant current and constant voltage) in the reverse order can also effect the desired result though the time of switching modes will be different. Also, one can divide the analysis time into more than two time segments and switch back and forth between the two modes more frequently. Constant power operation by itself is intermediate in its effect on migration time when compared to constant voltage and constant current operation. It can likewise be combined with one of the other two modes to eliminate migration time differences.

Further enhancement of the method involves the use of on-line migration time measurement and appropriate feedback control to determine optimum high voltage power supply switching times. This can be done by incorporating a reference peak into the separation such as by adding a minor component to the separation medium filling the capillary and the electrolyte reservoirs in FIG. 1. If indirect absorbance detection is being used, the minor component should be substantially nonabsorbing at the wavelength being used for detection. Conversely, if direct absorbance detection is used, the minor component should be absorbing at the measuring wavelength. The incorporation of the minor component will result in the appearance of a concentration peak at the detector at a migration time characteristic of the minor component. Alternatively, a known component could be added to the sample solution. If the minor component added to the separation medium or the known component added to the sample is chosen to produce a peak before most or all of the analyte peaks, then an on-line measure of the migration time of the reference peak can be directly measured and used to apply further correction. That is, the method detailed above can be used to determine migration times that are substantially independent of variations in sample conductivity. Any residual migration time change in the reference peak can be directly measured and used to apply a correction such as by initiating a further change of the high voltage power supply mode. This use of on-line feedback control provides second order correction which further eliminates migration time changes for the remaining sample components. For example, bromide is a rapidly migrating species in the analysis of anions by the method illustrated in FIGS. 2a-d. If bromide were added to the sample solution, a peak due to the bromide would be expected to be observed in the detector output at a given time point before the peaks for chloride and sulfate. If after use of the method of switching modes during the analysis run outlined above, a residual migration time shift for the known bromide concentration peak was detected, the measured time shift could be used to initiate another switching of mode to eliminate the residual migration time shift for the remaining peaks. That is if the bromide peak were detected at a point in time later than expected the power supply mode would be switched by the controller 30 back to constant current operation.

The present invention has been described in terms of constant voltage, current or power conditions. The term "constant" is intended to include substantially unvarying DC levels as well as any time varying waveform in which the average value of voltage or current measured over a complete cycle of the waveform remains substantially constant. Examples of such time varying waveforms, which are considered to be within the scope of the present invention, are the application of a pulsed voltage or current waveform to the capillary or the superimposition of an AC voltage or current on a DC separation voltage or current. Therefore, it is possible to use pulsed or AC modulated waveforms to obtain the same results in combining modes to eliminate migration time variations in the ways that we have previously described using substantially unvarying DC levels as long as the average value of these time varying waveforms, measured over a full cycle of the waveform, remains substantially constant for the duration of the time segment that mode is applied.

Although we have illustrated the method of the invention on the analysis of selected inorganic anions, it is apparent that the method will have applicability to other ions that can be analyzed by capillary electrophoresis. Furthermore, other variations of the invention will suggest themselves to those with ordinary skill in the art.

I claim:

1. A method for analyzing a sample by capillary electrophoresis with improved regularity of migration time comprising the steps of:
   dividing the analysis time into two or more time segments;
   applying to a capillary high voltage power in a first mode during a first time segment to effect separation of said sample;
   applying to said capillary high voltage power in a second and different mode during a subsequent time segment.

2. The method of claim 1 wherein said first and second modes are chosen among the group comprising: constant voltage, constant current and constant power.

3. A method for analyzing a sample by capillary electrophoresis with improved regularity of migration time comprising the steps of:
   dividing the analysis time into first and second time segments of predetermined length;
   applying to a capillary high voltage power in a constant voltage mode during the first time segment to effect separation of said sample;
   subsequently applying to said capillary high voltage power in a constant current mode during the second time segment.

4. A method for analyzing a sample by capillary electrophoresis with improved regularity of migration time comprising the steps of:
   dividing the analysis time into first and second time segments of predetermined length;
   applying to a capillary high voltage power in a constant current mode during the first time segment to effect separation of said sample;
   subsequently applying to said capillary high voltage power in a constant voltage mode during the second time segment.

5. A method as in claim 1 in which the high voltage power is applied in a constant power mode during said first time segment.

6. A method as in claim 3 in which the high voltage power is applied in a constant power mode during said second time segment.

7. A method as in claim 3 in which the high voltage power is applied in a constant power mode during said first time segment.

8. A method as in claim 1 in which the high voltage power is applied in a constant power mode during said second time segment.

9. A method for analyzing a sample solution introduced into a separation medium by capillary electrophoresis with improved regularity of migration time comprising the steps of:
   incorporating a reference peak in the separation medium or sample solution;
   applying to a capillary high voltage power in a first mode during a first time segment of the analysis to effect separation of said sample solution;
   applying high voltage power in a second and different mode during a subsequent time segment of the analysis;
   measuring the migration time of the reference peak;
   applying high voltage power in another mode based on the measured migration time of the reference peak.

10. The method of claim 9 wherein each of said modes are chosen among the group comprising: constant voltage, constant current and constant power.

11. A method for conducting an analysis of a sample by capillary electrophoresis comprising the steps of:
injecting a volume of the sample into a capillary;
applying the output of a power supply to the capillary in a first mode during a first time period within the analysis to effect separation of the sample;
initiating a change in the output of the power supply after said first time period to a second and different mode whereby changes in migration time of the sample are adjusted to substantially eliminate the effects of varying sample composition.

12. The method of claim 11 wherein said first mode is a constant current mode and said second mode is a constant voltage mode.

13. The method of claim 11 wherein said first mode is a constant voltage mode and said second mode is a constant current mode.